United States Patent [19]

Kuriyama et al.

[11] Patent Number: 5,159,091
[45] Date of Patent: Oct. 27, 1992

[54] PROCESS FOR PREPARING 21-DESOXYPREDNISOLONE 17-ESTERS

[75] Inventors: Tadatoshi Kuriyama, Yotsukaido; Masaki Ogawa, Narashino; Susumu Sato, Shisui; Naokata Taido, Funabashi; Tadayuki Kuraishi, Chiba, all of Japan

[73] Assignee: SS Pharmaceutical Co., Ltd., Tokyo, Japan

[21] Appl. No.: 596,323

[22] Filed: Oct. 12, 1990

[30] Foreign Application Priority Data

Oct. 26, 1989 [JP] Japan .................... 1-279188

[51] Int. Cl.$^5$ .......................... C07J 75/00; C07J 7/00
[52] U.S. Cl. ..................................... 552/569; 552/581
[58] Field of Search ................... 552/569, 581

[56] References Cited

U.S. PATENT DOCUMENTS 3,499,081 3/1970 Krakower et al. .............. 552/581
3,639,434 2/1972 Oxley et al. .................... 552/581
3,980,680 9/1976 Green ............................. 552/581

FOREIGN PATENT DOCUMENTS 2645104 4/1978 Fed. Rep. of Germany ...... 552/581

OTHER PUBLICATIONS

Carey and Sundberg Advanced Organic Chemistry Part A [N.Y., Plenum Press, 1984] pp. 212 to 215.
The Merck Index, 11th Ed. [Merck and Co., Rahway, N.J., 1989] p. 1358, entry 8533.
Chemical Abstracts, vol. 66, No. 7, Feb. 13, 1967, p. 2777, abstract No. 28973f, Columbus, Ohio, US; R. Vitali et al: "Substituted 17 alpha-hydroxyprogesterone esters. New synthetic routes and new derivatives", & Gazz. Chim. Ital. 96(8-9), 1115-24(1966).

Primary Examiner—Robert T. Bond
Assistant Examiner—E. C. Ward
Attorney, Agent, or Firm—Oblon, Spivak, McClelland, Maier & Neustadt

[57] ABSTRACT

A process for preparing 21-desoxyprednisolone 17-esters of formula (IV) is disclosed.

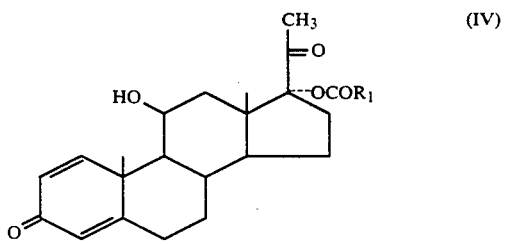

The process comprises reacting a prednisolone 17α,21-cyclic orthoester with an acid in a 40-60% lower alcohol solution to produce a prednisolone 17-ester, sulfonylating the prednisolone 17-ester into a prednisolone 17-ester 21-sulfonate, and reacting the sulfonate with an alkali metal iodide in methyl ethyl ketone in the presence of a lower fatty acid to produce the compound of formula (IV). The process ensures economical industrial production of high purity 21-desoxyprednisolone 17-esters, an excellent local anti-inflammatory medicine, in a high yield by simple procedures.

1 Claim, No Drawings

PROCESS FOR PREPARING 21-DESOXYPREDNISOLONE 17-ESTERS

BACKGROUND OF THE INVENTION

1. Field of the Invention

This invention relates to a novel process for industrially preparing 21-desoxyprednisolone 17-esters.

2. Description of the Background Art

21-Desoxyprednisolone 17-esters are compounds having a chemical structure of formula (IV),

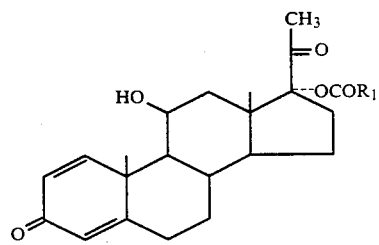
(IV)

wherein $R_1$ is a lower alkyl or aralkyl group. They are useful pharmaceutical compounds possessing an excellent local anti-inflammatory action (Japanese Patent Publication No. 20697-1971).

A number of processes are known for producing these compounds. All known processes, however, have drawbacks such as a low production yield, requirement of complicated purification procedures for eliminating 21-esters which are by-produced in these processes, and the like. None of them are suitable as a process for the industrial production of these compounds.

In view of this situation, the present inventors have undertaken extensive studies and have developed a novel process which is free from these drawbacks and can be applicable to industrial production of 21-desoxylorednisolone 17-esters.

SUMMARY OF THE INVENTION

Accordingly, an object of this invention is to provide a process for preparing a 21-desoxyprednisolone 17-ester represented by formula (IV),

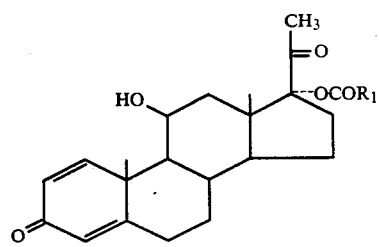
(IV)

wherein $R_1$ is a lower alkyl or aralkyl group, which comprises reacting a prednisolone 17α,21-cyclic orthoester of formula (I),

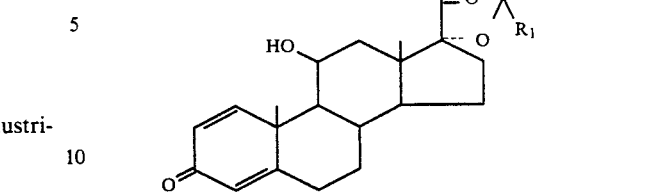
(I)

wherein $R_1$ has the same meaning as defined for formula (IV) and $R_2$ is a lower alkyl group, with an acid in a 40–60% lower alcohol solution to produce a prednisolone 17-ester of formula (II),

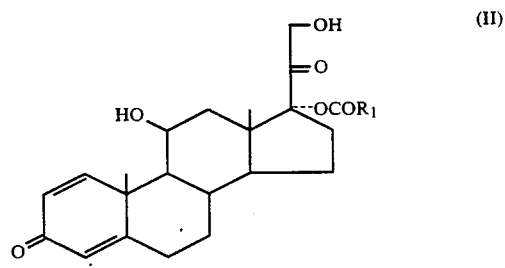
(II)

wherein $R_1$ has the same meaning as defined for formula (IV), sulfonylating the prednisolone 17-ester of formula (II) into a prednisolone 17-ester 21-sulfonate of formula (III),

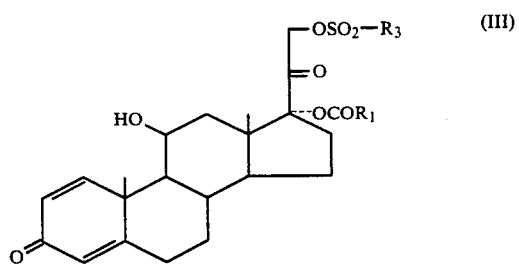
(III)

wherein $R_1$ has the same meaning as defined for formula (IV) and $R_3$ is a lower alkyl or aryl group, and reacting the prednisolone 17-ester 21-sulfonate of formula (III) with an alkali metal iodide in methyl ethyl ketone in the presence of a lower fatty acid.

Other objects, features and advantages of the invention will hereinafter become more readily apparent from the following description.

DETAILED DESCRIPTION OF THE INVENTION AND PREFERRED EMBODIMENTS

A lower alkyl group in this invention is defined as a lower or branched alkyl group having 1–6 carbon atoms such as methyl, ethyl, propyl, isopropyl, butyl, tert-butyl, or the like. A lower alcohol is defined as an alcohol having 1–6 carbon atoms such as methanol, ethanol, propanol, isopropanol, butanol, sec-tubanol, tert-butanol, pentanol, or the like. A lower fatty acid is defined as a fatty acid having 1–6 carbon atoms such as acetic acid, proopionic acid, or butyric acid.

The reactions in the process of this invention proceeds as follows:

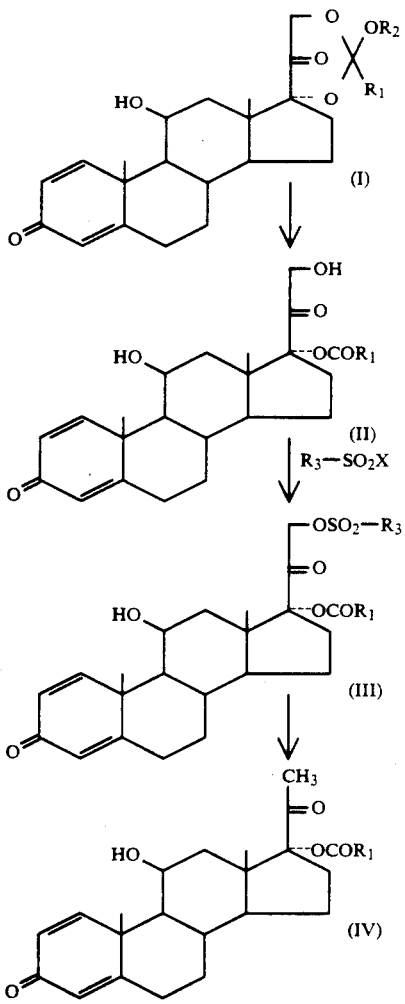

wherein $R_1$ is a lower alkyl or aralkyl group, $R_2$ is a lower alkyl group, $R_3$ is a lower alkyl or aryl group, and X is a halogen atom.

The process comprises reacting a prednisolone 17α,21-cyclic orthoester of formula (I) with an acid in a 40–60% lower alcohol solution to produce a prednisolone 17-ester of formula (II), sulfonylating the compound of formula (II) into a prednisolone 17-ester 21-sulfonate of formula (III), and reacting the sulfonate of formula (III) with an alkali metal iodide in methyl ethyl ketone in the presence of a lower fatty acid to produce a 21-desoxyprednisolone 17-ester of formula (IV).

The raw material which is a compound of formula (I) is a known compound and can be prepared, for example, from prednisolone by a known process.

An outstanding feature in the process of the present invention is in the use of a 40–60% lower alcohol solution as a solvent in the reaction producing compound (II) from compound (I). The use of solvent reduces by-production of 21-ester compounds and ensures selective production of 17-ester compounds. Boric acid, p-toluenesulfonic acid, maleic acid, oxalic acid, or the like can be used as an acid. The reaction proceeds at room temperature to 80° C. A desirable reaction time is 30 minutes to 4 hours. The reaction using boric acid as an acid in about 50% ethanol at a temperature of 60 to 80° C for 2 to 4 hours is particularly preferable.

A conventional sulfonylation process can be used for converting compound (II) into compound (III). The reaction of compound (II) with a sulfonyl halogenide, for example, in the presence of a base can produce compound (III) in a high yield.

A feature in the reaction for producing compound (IV) from compound (III) is in the use of methyl ethyl ketone as a solvent and effecting the reaction in the presence of a lower fatty acid. Acetic acid, propionic acid, butyric acid, and the like can be given as lower fatty acids which can be used in the reaction A use of a lower fatty acid in an amount of 1/20 to 1 mole for compound (III) is preferable. 21-Iodide may be by-produced in the absence of a fatty acid, resulting in the requirement of complicated purification procedures and reduced yield. Sodium iodide or potassium iodide can be used as an alkali metal iodide. It is desirable that the reaction be carried out at the boiling point of methyl ethyl ketone under refluxing.

High purity 21-desoxyprednisolone 17-esters can be prepared by the process of the present invention in a high yield using simple procedures. Thus, the process is highly advantageous as an industrial production of 21-desoxyprednisolone 17-esters.

Other features of the invention will become apparent in the course of the following description of the exemplary embodiments which are given for illustration of the invention and are not intended to be limiting thereof.

EXAMPLES

Example 1

Preparation of prednisolone 17-propionate 0.5 g of boric acid was added to a suspension of 8 g of prednisolone 17,21-ethylorthopropionate in 100 ml of 50% ethanol, and the mixture was heated for 2 hours at 75° C. After completion of the reaction, 25 ml of water was added to the resultant reaction mixture, followed by cooling with ice water. The resultant precipitate was collected on a filter, washed with water, and dried to obtain 6.75 g (yield: 90%) of colorless crystals of the title compound. mp: 213°–216° C.

Example 2

Preparation of prednisolone 17-propionate

To a solution of 2.22 g of prednisolone 17,21-ethylorthopropionate in 50 ml of ethanol was added 50 ml of water. After an addition of 0.25 ml of 1M p-toluenesulfonic acid aqueous solution at room temperature while stirring, the mixture was stirred for 30 minutes. After the reaction, the resultant reaction mixture was filtered to separate precipitated insolubles. Water was added to the filtrate, followed by extraction with chloroform. The chloroform extract was dried over anhydrous sodium sulfate. After evaporating the chloroform, the residue was recrystallized from a water-ethanol mixture to obtain 1.8 g (yield: 86%) of colorless crystals of the title compound.

Example 3

Preparation of prednisolone 21-methanesulfonate 17-propionate

To a solution of 4.9 g of prednisolone 17-propionate in 11 ml of pyridine was added dropwise 2.4 g of methanesulfonyl chloride under ice-cooling while stirring. The mixture was stirred for a further 2 hours. After the reaction, the resultant reaction mixture was poured into 100 ml of ice-water, stirred for 30 minutes, and filtered to collect precipitated crystals The crystals were thoroughly washed with water, and recrystallized from 90 ml of ethanol to obtain 5.3 g (yield: 91%) of colorless needles of the title compound mp: 135°–137° C.

Example 4

Preparation of 21-desoxyprednisolone 17-propionate 2 g of prednisolone 21-methanesulfonate 17-propionate, 130 m9 of aoetic acid, and 2 9 of sodium iodide were dissolved into 20 ml of methyl ethyl ketone. The mixture was refluxed for 6 hours. After completion of the reaction, methyl ethyl ketone was evaporated under reduced pressure. To the residue was added 2.2 g of sodium thiosulfate in 20 ml water to collect precipitated crystals by filtration. The crystals were thoroughly washed with water and dried to obtain 1.52 g (yield: 94%) of colorless powder of the title compound. mp: 224°–227° C.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing a 21-desoxyprednisolone 17-ester represented by formula (IV),

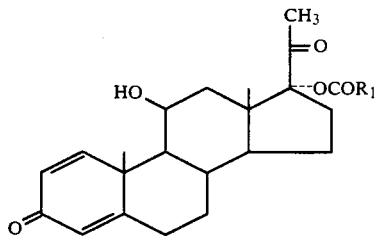

wherein $R_1$ is a lower alkyl or aralkyl group, which comprises reacting a prednisoone 17α,21-cyclic orthoester of formula (I),

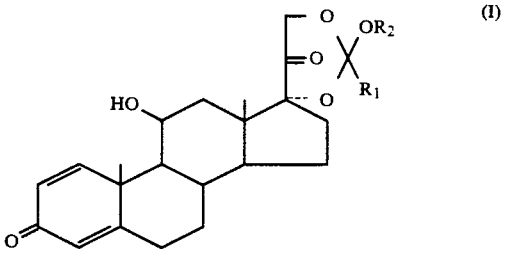

wherein $R_1$ has the same meaning as defined for formula (IV) and $R_2$ is a lower alkyl group, with boric acid in a 40–60% lower alcohol solution to produce a prednisolone 17-ester of formula (II),

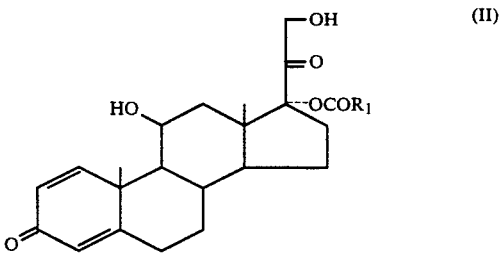

wherein $R_1$ has the same meaning as defined for formula (IV), sulfonylating the prednisolone 17-ester of formula (II) into a prednisolone 17-ester 21-sulfonate of formula (III),

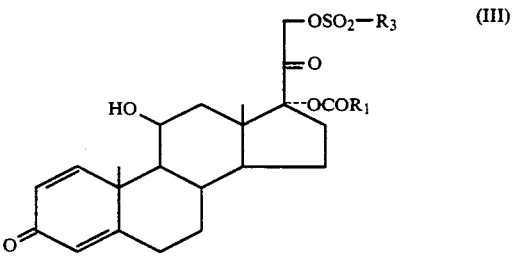

wherein $R_1$ has the same meaning as defined for formula (IV) and $R_3$ is a lower alkyl or aryl group, and reacting prednisolone 17-ester 21-sulfonate of formula (III) with an alkali metal iodide in methyl ethyl ketone in the presence of a lower fatty acid.

* * * * *

UNITED STATES PATENT AND TRADEMARK OFFICE
CERTIFICATE OF CORRECTION

PATENT NO. : 5,159,091

DATED : October 27, 1992

INVENTOR(S) : Tadatoshi Kuriyama et al

It is certified that error appears in the above-identified patent and that said Letters Patent is hereby corrected as shown below:

Column 5, line 51, correct "prednisoone" to read --prednisolone--.

Signed and Sealed this

Fifth Day of October, 1993

*Attest:*

BRUCE LEHMAN

*Attesting Officer*     *Commissioner of Patents and Trademarks*